(12) United States Patent
Guidotti et al.

(10) Patent No.: US 7,235,708 B2
(45) Date of Patent: Jun. 26, 2007

(54) ABSORBENT ARTICLE COMPRISING AN ABSORBENT STRUCTURE

(75) Inventors: Ted Guidotti, Gothenburg (SE); Ing-Britt Magnusson, Molnlycke (SE); Madeleine Pehrson, Molnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 279 days.

(21) Appl. No.: 10/807,423

(22) Filed: Mar. 24, 2004

(65) Prior Publication Data

US 2004/0193129 A1 Sep. 30, 2004

Related U.S. Application Data

(60) Provisional application No. 60/457,314, filed on Mar. 26, 2003.

(51) Int. Cl.
*A61F 13/534* (2006.01)
*A61F 13/537* (2006.01)

(52) U.S. Cl. .................. 604/369; 604/368; 604/380

(58) Field of Classification Search ............... 604/369, 604/378, 383, 367, 368, 380
See application file for complete search history.

(56) References Cited

U.S. PATENT DOCUMENTS

| | | | | |
|---|---|---|---|---|
| 3,934,588 A | * | 1/1976 | Mesek et al. ............... 604/365 |
| 4,232,674 A | * | 11/1980 | Melican ...................... 604/369 |
| 4,239,043 A | * | 12/1980 | Gellert ........................ 604/15 |
| 4,394,930 A | * | 7/1983 | Korpman .................. 220/62.18 |
| 4,500,315 A | * | 2/1985 | Pieniak et al. .............. 604/379 |
| 4,560,372 A | * | 12/1985 | Pieniak ....................... 604/369 |
| 4,664,662 A | * | 5/1987 | Webster ....................... 602/47 |
| 5,338,766 A | | 8/1994 | Phan et al. |
| 5,500,270 A | * | 3/1996 | Langdon et al. ............ 428/119 |
| 5,643,238 A | * | 7/1997 | Baker .......................... 604/368 |
| 5,713,881 A | * | 2/1998 | Rezai et al. ................. 604/368 |
| 5,762,641 A | * | 6/1998 | Bewick-Sonntag et al. . 604/378 |
| 5,817,704 A | | 10/1998 | Shively et al. |
| 5,941,863 A | * | 8/1999 | Guidotti et al. ............. 604/378 |
| 6,103,358 A | * | 8/2000 | Bruggemann et al. ... 428/317.9 |
| 6,203,654 B1 | * | 3/2001 | McFall et al. .............. 156/268 |
| 6,657,101 B1 | * | 12/2003 | Malmgren et al. .......... 604/367 |
| 6,972,011 B2 | * | 12/2005 | Maeda et al. .......... 604/385.01 |
| 2003/0135177 A1 | * | 7/2003 | Baker ......................... 604/368 |

FOREIGN PATENT DOCUMENTS

| | | |
|---|---|---|
| EP | 0 615 736 | 2/1994 |
| EP | 0 532 002 | 5/1997 |
| EP | 0 443 627 | 6/1997 |
| WO | 99/55393 A1 | 11/1999 |
| WO | 01/15649 A1 | 3/2001 |
| WO | WO 2004/007598 A1 | 1/2004 |

* cited by examiner

*Primary Examiner*—Tatyana Zalukaeva
*Assistant Examiner*—Paula L. Craig
(74) *Attorney, Agent, or Firm*—Buchanan Ingersoll & Rooney, PC

(57) ABSTRACT

The invention relates to an absorbent article, such as a diaper, an incontinence guard, a sanitary napkin or the like, including a liquid-permeable upper surface and an absorbent structure exhibiting a planar extension. The absorbent structure includes an acquisition layer and at least one storage layer. The acquisition layer has a plurality of fragments of a liquid-absorbing, open-celled, polyacrylate-based foam material, and each fragment exhibits a planar extension having a transversal direction, a longitudinal direction, and a thickness direction extending perpendicularly to the planar extension. The width in the transversal direction of each fragment in a dry condition does not exceed 10 millimeters, and the total area of the fragments in the planar extension is lower than the area of the absorbent structure in the planar extension.

10 Claims, 2 Drawing Sheets

ABSORBENT ARTICLE COMPRISING AN ABSORBENT STRUCTURE

CROSS-REFERENCE TO RELATED APPLICATIONS

This application claims priority to U.S. Provisional Application Ser. No. 60/457,314 entitled "Absorbent Article Comprising an Absorbent Structure," filed on Mar. 26, 2003, the entire content of which is hereby incorporated by reference and relied upon in its entirety.

FIELD OF THE INVENTION

The present invention relates to an absorbent article, such as a diaper, an incontinence guard, a sanitary napkin or the like, whereby the article exhibits a liquid-permeable upper surface and comprises an absorbent structure, exhibiting a planar extension, wherein the absorbent structure comprises an acquisition layer and at least one storage layer.

BACKGROUND OF THE INVENTION

Absorbent articles such as diapers, incontinence guards, sanitary napkins, intended for one single use, usually comprise an absorbent structure having the capability to acquire large amounts of liquid under a short period of time, and further having the ability to distribute the liquid and to store the liquid. This means that the absorbent structure usually comprises several different layers having different properties with respect to each other. Frequently, the absorbent structure at least comprises a liquid acquisition layer and a liquid storage layer. The liquid storage layer often comprises a cellulosic fluff pulp layer mixed with a superabsorbent material, which are polymers having the ability to absorb many times their own weight of water or bodily fluids. The liquid acquisition layer often comprises a porous fibrous layer of synthetic fibers.

Upon usage of such absorbent articles, it is desirable that they are thin and discreet to wear, and that they at the same time rapidly can acquire a large amount of liquid discharged during a short period of time and then store this liquid in the article.

However, it has been shown that it is difficult to obtain sufficient liquid-acquiring capacity, liquid distribution capacity and liquid storage capacity for products, which at the same time are thin and discreet to wear.

In order to obtain a thin product, it is previously known to use a relatively high percentage of a superabsorbent material in the absorbent structure. For example, as shown in EP 0 532 002 and EP 0 615 736, it is known to use an absorbent structure for use in a diaper containing at least 30 percent by weight or more of a superabsorbent material. It is further known from EP 0 443 627 to use an absorbent structure containing 60 percent by weight of a superabsorbent material.

However, it has been shown to be difficult to obtain a thin absorbent article exhibiting an optimal combination of sufficiently high liquid-acquiring capacity, sufficient local and total absorption capacity and sufficient liquid transport ability. It is further important, mainly for diapers and incontinence guards, that the article upon repeated wettings is able to receive and absorb relatively large amounts of liquid discharged during a short period of time.

SUMMARY

According to embodiments of the present invention, an article has been provided, which is thin and discreet to wear, and at the same time exhibits sufficient liquid-acquiring capacity, liquid distribution capacity and liquid storage capacity.

In an absorbent article according to an embodiment of the invention, the acquisition layer comprises a plurality of fragments of a liquid-absorbing open-celled polyacrylate-based foam material, wherein each fragment exhibits a planar extension having a longitudinal direction and a transversal direction, and a thickness direction extending perpendicularly to the planar extension, wherein the width in the transversal direction on each fragment in a dry condition, does not exceed 10 millimeters and that the total area of the fragments in the planar extension is less than the total area of the absorbent structure in the planar extension. Because the acquisition layer comprises a plurality of separate fragments, where at least most fragments are arranged with a distance to each other, a free space between the fragments is obtained. Accordingly, the fragments can expand unhindered. Due to the free spaces between the fragments, the foam fragments have thereby the ability to expand in three dimensions upon wetting, i.e., in all three planes of the fragments.

According to one embodiment, the width of the fragments is not more than 7.0 millimeters, and more preferably, not more than 6.0 millimeters.

According to one embodiment, each fragment exhibits in a dry condition a length, i.e., in the longitudinal direction of the fragments, which does not exceed 20 millimeters, or more preferably, not more than 10 millimeters.

Upon storage of absorbent articles in a sealed diaper package, the thickness of the fragments is preferably below 2 millimeters. The term "diaper package" denotes the package in which the diapers are enclosed when selling the diapers. In some cases, the diapers are packed one by one, whereby a number of single-wrapped diapers then are further enclosed in a bigger package. Thus, the term "diaper package" does not denote the single-wrapped diaper, but the bigger diaper package. Analogously, when the absorbent article is an incontinence guard or a sanitary napkin, the thickness of the fragments is referred to as the exhibited thickness in the absorbent structure comprised in the articles within a sealed package for incontinence guards or sanitary napkins. Upon measurement of the thickness of the fragments, the measurement is performed within 2 minutes after opening the package in question.

In preferred embodiments, the fragments are obtained in such a way that a plurality of parts, i.e., fragments, are cut out from a compressed foam layer. Thus, the thickness of the fragments in a dry condition is equal to the thickness of the compressed foam layer in a dry condition. The polyacrylate-based foam material is highly compressed in a dry condition, such that it expands heavily upon wetting. The fragments may be cut out in such a way so that they substantially exhibit a rectangular shape.

According to an alternative way to produce the fragments, the foam is dripped into separate drops and the foam structure is then cross-linked, compressed, and dried. Upon such production of the fragments, the fragments obtain a circular or oval shape.

According to one embodiment, the total area of the fragments in the planar extension is maximally 50% of the total area of the absorbent structure in the planar extension.

According to yet another embodiment, the total area of the fragments in the planar extension is maximally 30% of the total area of the absorbent structure in the planar extension.

It is also possible that some portions of the absorbent structure exhibit a plurality of fragments, while other portions of the absorbent structure are essentially free from fragments. For example, it is possible that the fragments are arranged against the upper surface of the absorbent structure in the crotch portion, while the two end portions at least substantially are free from fragments. However, according to that embodiment, single fragments may appear outside the portion intended to contain fragments. In an embodiment having one or more portions with fragments, it is the total area of the fragments in the planar extension which preferably maximally is 50% of the total area in the planar extension. The size of a portion having fragments is estimated in the following way. The closest distance to an adjacent fragment is not larger than five times the width of the fragment. If the closest distance to an adjacent fragment is more than five times the width of this fragment, the fragment in question does not belong to the part being the area of the portion.

According to a further embodiment, the total area of the fragments in a portion is maximally 30% of the total area of the absorbent structure in such portion.

According to another embodiment, the free space between several fragments is at least twice as large as the width of the fragments. The free space between the fragments, i.e., the distance between fragments, is measured between the outer edges of the fragments. The term "several fragments" denotes at least 70% of the total number of fragments, and more preferably, at least 80% of the total number of fragments.

It has shown to be especially advantageous to design the absorbent structure in such a way that the foam fragments are located in the portion being closest to the user, i.e., in the portion being the first one to be wet. The advantage using such an acquisition layer, is that it is able to receive a large amount of liquid in a short period of time. The cell walls in the foam fragments expand heavily upon wetting. When the cell walls of the foam material expand, the volume in the pores heavily increases. The liquid absorbed by the pores is very loosely bound and can be drained by a underlying layer having higher capillary forces. Consequently, the acquisition layer can receive a second dose of liquid, i.e., a new dose of liquid discharged during a short period of time.

The part of the liquid absorbed by the cell walls is more tightly bound than the loosely bound liquid absorbed by the pores. It has been proved to be an advantage that a certain amount of the liquid is absorbed by the cell walls and thereby is tightly bound. The risk is then smaller than for other acquisition layers that the surface closest to the user is wetted.

Upon storage of absorbent articles in a sealed diaper package, the thickness of the fragments is preferably exceeding 0.50 g/cm$^3$. The term "diaper package" denotes the package, in which the diapers are enclosed when selling the diapers. In some cases, the diapers are packed one by one, whereby a number of single-packed diapers then are further enclosed in a bigger package. The term "diaper package" does not denote a singly-packed diaper but the bigger diaper package. Analogously, when the absorbent article is an incontinence guard or a sanitary napkin, the density of the fragments is referred to as the exhibited density in the absorbent structure comprised in said articles within a sealed package for incontinence guards or sanitary napkins. Measurements of the density of the fragments is made within 2 minutes after opening the package in question.

According to one embodiment, the volume of each fragment increases by at least 500% upon wetting.

According to another embodiment, the area in the planar extension of each fragment upon wetting increases by at least 300%.

The polyacrylate-based superabsorbent foam material is produced by the saturation under pressure using carbon dioxide of a solution, which at least contains monomer, a cross-linking material, an initiator, and a tenside in a vessel. When the solution is removed from the vessel through a nozzle, the solution is expanded and a foamed structure is achieved. The foamed structure is then locked in that polymerization and cross-linking are initiated by for instance UV radiation and/or e-beam. Finally, the material is compressed and dried.

It has been shown that the plurality of fragments can be applied and maintained against a surface without the need of applying any kind of adherent material.

It is also possible to apply the fragments of the superabsorbent foam material, i.e., the acquisition layer, between two storage layers. The fragments can be applied equally distributed over the entire surface of the storage layer, solely in the crotch portion or intermittently in some portions, such as, e.g., in longitudinally- or transversally-extending strands.

According to an embodiment of an absorbent article, the storage layer comprises cellulosic fibers and a particulate superabsorbent material, wherein the amount particulate superabsorbent material, calculated on the total weight of the storage layer in a dry condition is at least 50 percent by weight. The percentage superabsorbent material calculated on the total weight of the storage layer in a dry condition can be higher, such as at least 60 percent by weight or at least 70 percent by weight. In order to create a thin article, which is discreet and comfortable to wear and which exhibits a sufficiently high absorption capacity, it has been shown that it is advantageous to use a high percentage of the superabsorbent material in the storage layer.

DETAILED DESCRIPTION OF PREFERRED EMBODIMENTS

Figure 1:
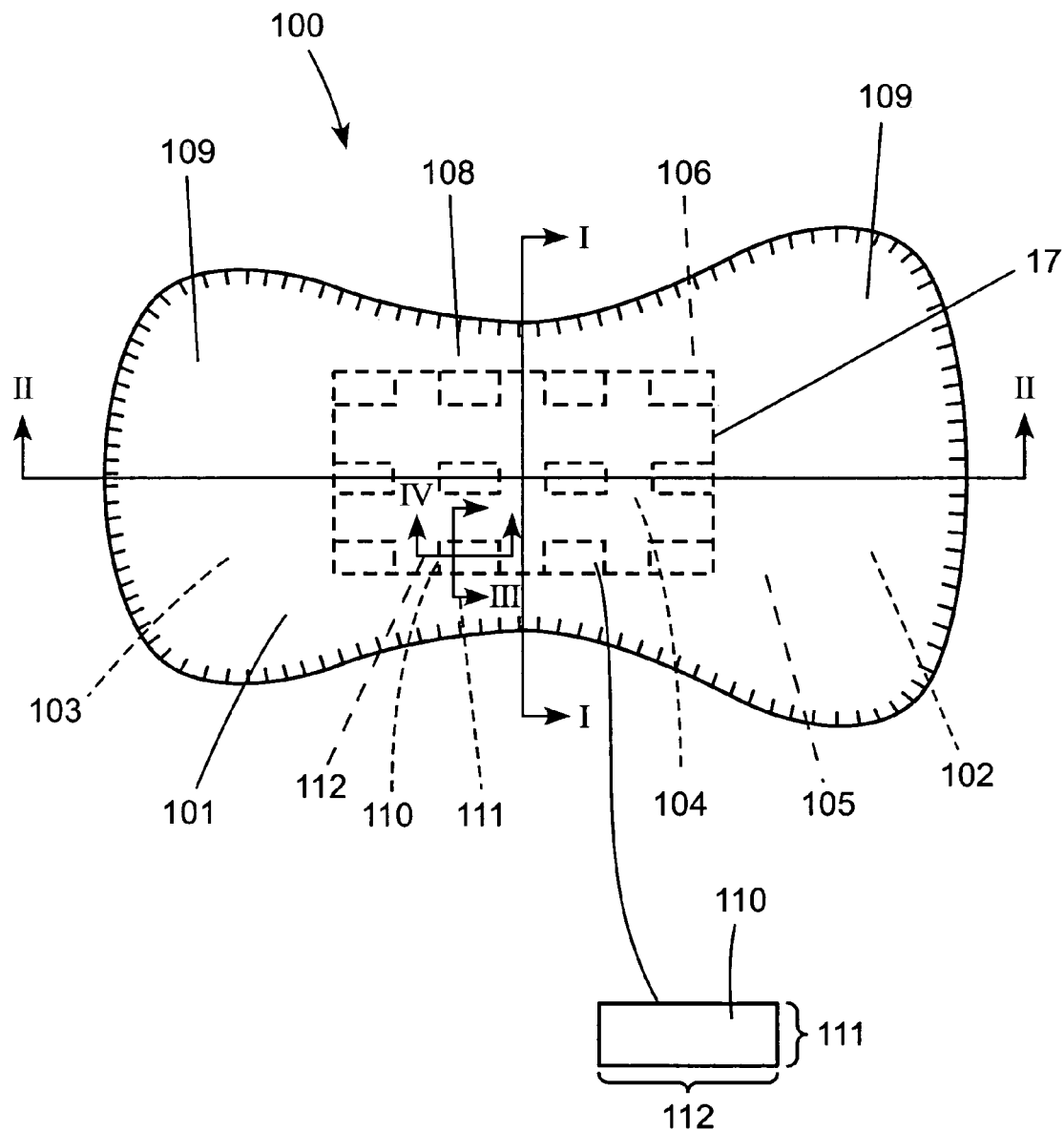
FIG. 1 shows a planar view of an absorbent article according to an embodiment of the invention.

The following description refers to embodiments of absorbent articles according to the invention, which is not limited to the below-described embodiments. In FIG. 1, a planar view of an absorbent article 100 according to an embodiment of the invention is shown. The absorbent article 100 exhibits a transversal direction, being shown by a transversally-extending center line I, and a longitudinal direction being shown by a longitudinally-extending center line II. Further, the absorbent article 100 exhibits a thickness direction, being perpendicular to the plane. The absorbent article 100 has a liquid-permeable top sheet 101, which during use of the article is intended to lie closest to the user. Further, the absorbent article 100 has a back sheet 102, which is at least substantially liquid-impermeable, and an absorbent structure 103 enclosed between the liquid-permeable top sheet and the back sheet. The back sheet material 102 may optionally be a so called vapor-permeable breathable material. The absorbent structure 103 comprises an acquisition layer 104, which is intended to rapidly receive a large amount of liquid and a first storage layer 105, which is intended to rapidly store a large amount of liquid, and a second storage layer 106. The second storage layer 106 has a longer extension in the plane of the article than the first storage layer 105, but exhibits a lower total absorption capacity. The second storage layer also functions as a form-rendering element in such way that it assists in creating and maintaining an absorbent structure being flexible against the body.

The storage layers 105, 106 may comprise optional absorbent materials, such as fibrous materials, foam materials, superabsorbent polymers, and combinations thereof. According to one embodiment, the first storage layer 105 is a fibrous structure comprising a relatively high proportion, preferably at least 50 percent by weight of a superabsorbent material calculated on the total weight of the first storage layer 105. Superabsorbent materials are polymers having the capability to absorb many times their own weight of water or bodily fluids. The superabsorbent material may be present in the form of powder, flakes, fibers, granules, or the like. The superabsorbent material in the storage layer 105 may be mixed with the fiber material or may be applied as one or more layers between fiber layers. The super absorbent material may be equally distributed in the first storage layer 105 or distributed in various concentrations in the longitudinal and/or the thickness direction of the first storage layer 105.

In one embodiment, the second storage layer 106 is preferably thinner than the first storage layer 105. The second storage layer 106 can, according to an embodiment, comprise a fibrous structure containing superabsorbent material. The percentage superabsorbent material in the second storage layer 106 is preferably lower than the amount of superabsorbent material in the first storage layer 105. For example, the second storage layer 106 may comprise about 10 percent by weight of a super absorbent material calculated on the total weight of the second storage layer 106. The second storage layer 106 has a longer extension in the plane of the article, but exhibits a lower total absorption capacity. The liquid-permeable top sheet 101 may be a nonwoven material or an apertured plastic film, or a laminate thereof. Examples of polymers of which the liquid-permeable top sheet can be made of include, but are not limited to, polyethylene, polypropylene, polyester, or copolymers thereof. To enable the liquid-permeable top sheet 101 to rapidly let the discharged bodily fluid through, the top sheet is often coated with tensides and/or is apertured.

In one embodiment, the acquisition layer 104 may comprise a plurality of fragments 110 made of an open-celled, polyacrylate-based foam material, wherein each fragment 110 exhibits a planar extension, exhibiting a longitudinal direction being shown by a longitudinally extending center line IV, and a transversal direction being shown by a transversally extending center line III. Further, each fragment 110 exhibits a thickness direction being perpendicular to the planar extension. The width 111 in the transversal direction on each fragment 110 in a dry condition, preferably does not exceed 10 millimeters. The fragments 110 of the acquisition layer 104 further exhibit a length 112, which preferably does not exceed 20 millimeters. The fragments 110 in the acquisition layer 104 are arranged in a portion of the crotch portion 108 of the absorbent structure between the end portion 109. The outermost fragments in the portion containing the fragments determine the total area of the portion. In order to determine the area of that portion of the absorbent structure, a line is drawn between the outer edges of outermost fragments. This portion is indicated with a dotted line 17 in FIG. 1.

Figure 2:
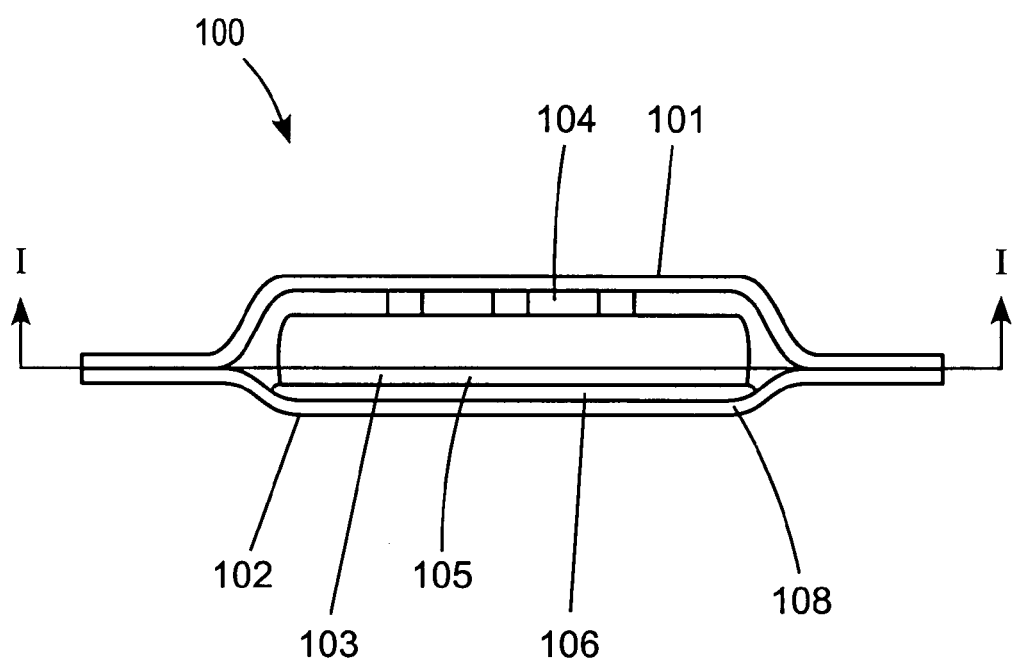
FIG. 2 shows a cross-section of the absorbent article shown in FIG. 1.

FIG. 2 shows a cross-section in the crotch portion 108 of the absorbent article 100 shown in FIG. 1. Thus, the absorbent article 100 has a liquid-permeable top sheet 101, which during use of the article is intended to lie closest to the user, a substantially liquid-impermeable back sheet 102, and an absorbent structure 103 enclosed therebetween. The absorbent structure 103 comprises an acquisition layer 104, which is arranged closest towards the liquid-permeable top sheet 101, a first storage layer 105, and a second storage layer 106. The first storage layer 105, is arranged between the acquisition layer 104 and the second storage layer 106. The second storage layer 106 is arranged between the first storage layer 105 and the backsheet 102. The construction of the different layers is described in detail in the above description of FIG. 1.

Figure 3:
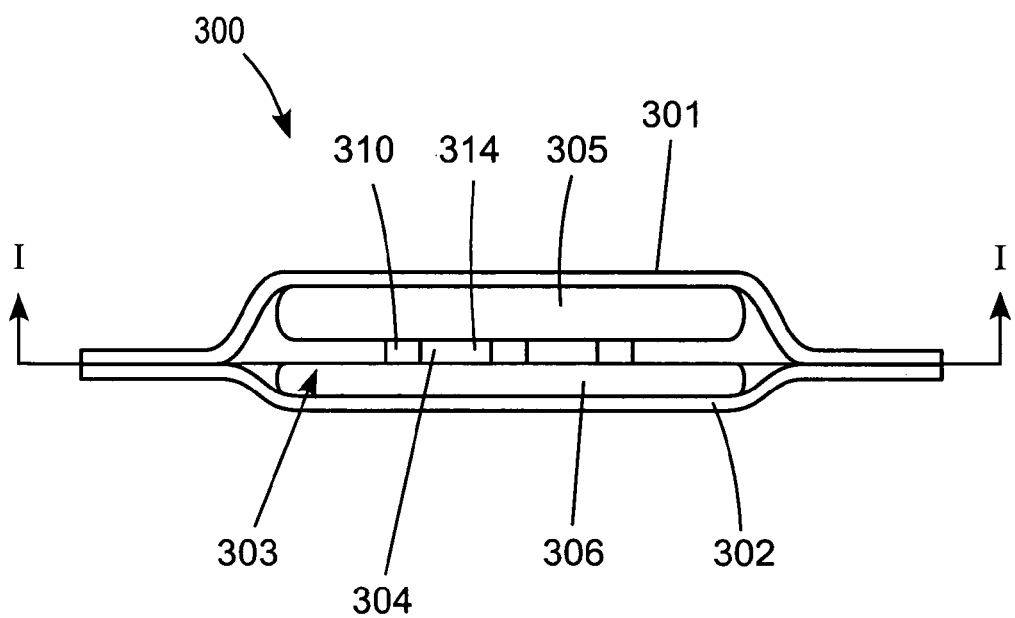
FIG. 3 shows a cross-section of an alternative embodiment of an absorbent article according to the invention.

FIG. 3 shows a cross-section along a transversally-extending center line I of an alternative embodiment of an absorbent article 300 according to the invention. The absorbent article 300 has a liquid-permeable top sheet 301, which during use of the article 300 is intended to lie closest to the user, a substantially liquid-impermeable back sheet 302, and an absorbent structure 303 enclosed therebetween. An acquisition layer 304 comprises three separate fragments 310. The fragments are constituted of strips extending in the longitudinal direction of the article. Between the strips, there is a space being free from the acquisition material, i.e., a hollow space, 314. Preferably the strips comprise a superabsorbent foam material. Upon wetting, such a superabsorbent expands heavily in all directions of the material. Thus, the hollow spaces 314 render space for the super absorbent foam material to expand without substantially changing the shape of the absorbent structure.

The storage layer is divided in an upper and a lower storage layer 305 and 306, at which the acquisition layer 304 is placed between these two layers. The upper and the lower storage layers may be of the same material compositions as has been stated above with respect to the storage layers 105 and 106 in FIG. 1. The material composition can be the same in the two layers 305 and 306, or it can be different, e.g., the content of cellulosic fluff pulp and superabsorbent material may be different in the different layers.

EXAMPLES

Example 1

Measurements of the Expansion of Foam Materials

Upon measurement of the expansion in the thickness direction of the materials, samples were cut out having a known diameter. The dry diameter ($d_d$) and the dry thickness ($t_d$) were measured. The samples were then allowed to swell in a NaCl solution (0.9 grams by weight of NaCl). Thereafter, the wet diameter ($d_w$) and the wet thickness ($t_w$) were measured. The expansion of the thickness (TE) expressed in percentage, the expansion of the area (AE) expressed in percentage and the expansion of the volume (VE) expressed in percentage, were then estimated using the formulas below.

$$TE = (t_w - t_d)/t_d * 100$$

$$AE = (d_w 2 - d_d 2)/d_d 2 * 100$$

$$VE = (t_w d_w 2 - t_d d_d 2)/t_d d_d 2 * 100$$

The tested materials are a polyacrylate-based foam material, denoted Foam XII. Foam XII has been made according to the following description:

To a beaker, the following is added:

348.5 grams of acrylic acid (4.84 moles)

135.5 grams of a sodium acrylate solution containing 37.3 percent per weight (0.54 moles) 28.0 grams of polyethylene glycol diacrylate from polyethylene glycol having a molecular weight of 400.

21.3 grams of an aqueous solution 15 percent per weight containing ethylene oxide and linear $C_{16}$–$C_{18}$ fatty alcohol (molar ratio 80:1)

65.7 grams of water.

The ingredients were mixed and thereafter, the solution was cooled to a temperature lower than 16° C. The solution was then poured into a closed container, whereby the solution was saturated with carbon dioxide at a pressure of 12 bar for 25 minutes. Using the same pressure, 26.7 grams of an aqueous solution containing 3 percent by weight of 2,2'-azobis (2-amidinopropane) dihydrochloride. This was mixed to a homogenous solution. The solution was then allowed to rest for five minutes. The saturated solution was compressed from a container using a nozzle having an opening of 1 mm at a pressure of 12 bar.

The resulting monomeric foam was placed on a glass plate (DIN-A3). An additional glass plate was then placed on top of the monomeric foam. Then, the foam was polymerized using a UV/VIS lamp, a UV1000 lamp from Höhnle. The foam was illuminated using the lamp both from underneath and from above. The illumination and thereby also the polymerization was allowed to proceed for 4 minutes.

TABLE 1

| $d_d$ | $t_d$ (s) | $d_w$ | $t_w$ (s) | TE | AE | VE |
|---|---|---|---|---|---|---|
| 28 | 3.8 | 62 | 6 | 58 | 357 | 622 |
| 28 | 3.8 | 61 | 6 | 58 | 390 | 577 |
| 28 | 3.8 | 62 | 6 | 58 | 390 | 649 |

The thickness expansion is preferably 40–80%, the area expansion is preferably 300–400% and the volume expansion is preferably 500–700%.

Example 2

Estimation of the Time Required for an Absorbent Article to Absorb a Predetermined Amount of Liquid Measurements have been performed to determine the time required for five different absorbent articles to absorb 100 ml of synthetic urine. Further, the time required for an additional second and third liquid dose to be absorbed was also measured, which corresponds to a second and third wetting, respectively.

All five absorbent articles comprise a top sheet, acquisition layer, storage layer and backsheet. Because the measurement related to the time required for the absorbent article to absorb a predetermined amount of liquid, the tested articles did not exhibit any elastic means or fastening means. Thus, it is the function of the topsheet and the absorbent structure which is being tested. The top sheet in all five tested articles is made of a carded nonwoven material of polypropylene denoted Novelin 650, from JW Suominen OY. The grammage is 23 g/m². The back sheet consists in all five tested articles of a polypropylene film.

Tested Absorbent Article No. 1

The absorbent structure comprises an acquisition layer containing a plurality of fragments of Foam XII. The fragments have a width being 5 mm and a length of 7 mm. The total weight of the fragments, i.e., the weight of the acquisition layer, is 2.08 grams, which during manufacture may vary by 0.01 grams. The acquisition layer is arranged between the liquid permeable top sheet and the storage layer. The storage layer comprises a first storage layer and a second storage layer. Both the first storage layer and the second storage layer consist of cellulosic fluff pulp and a particulate polyacrylate-based superabsorbent material. The cellulosic fluff pulp in the first storage layer is a chemically manufactured pulp from Weyerhauser and is denoted NB 416. The cellulosic fluff pulp is formed in three different layers, wherein the layers have a grammage being 100 g/m², 50 g/m² and 100 g/m², respectively. The particulate superabsorbent material is a polyacrylate-based superabsorbent material. The particulate superabsorbent material is applied between the cellulosic layers, whereby the superabsorbent then has two separate layers. Each layer of the particulate superabsorbent material exhibits a grammage being 275 g/m². The second storage layer comprises a chemically manufactured pulp and polyacrylate-based superabsorbent material. The superabsorbent is mixed in the cellulosic fluff pulp. The percentage of superabsorbent material in the second storage layer is 10 percent by weight. The total grammage of the second storage layer is 200 g/m².

Tested Absorbent Article No. 2

The absorbent structure comprises an acquisition layer containing a layer of Foam XII. The acquisition layer has a width being 6 cm and a length of 13 cm, and the total weight of the acquisition layer is 6.25 grams. The acquisition layer is arranged between the liquid-permeable top sheet and the storage layer. The storage layer comprises the same structure as the storage layer of the tested absorbent article No. 1.

Tested Absorbent Article No. 3

The absorbent structure comprises an acquisition layer containing a plurality of fragments of Foam XII. The acquisition layer is arranged between two different layers of storage material. The storage layer comprises the same structure as the storage layer of the tested absorbent article No. 1.

Tested Absorbent Article No. 4

The absorbent article comprises an acquisition layer containing a layer of Foam XII, wherein the acquisition layer is arranged between two different layers of storage material. The storage layer comprises the same structure as the storage layer of the tested absorbent article No. 1.

Tested Absorbent Article No. 5

Finally, an article was tested that did not contain any acquisition layer. The absorbent article consisted of a storage layer, which was constructed in the same way as the storage layer of the tested absorbent article No. 1.

The time required to absorb 100 ml of synthetic urine was measured. Further, the time required for an additional second and third liquid dose to be absorbed was also measured, which corresponds to a second and third wetting, respectively.

TABLE 2

| | Absorption time (s) | | | | |
|---|---|---|---|---|---|
| Wetting | Art. 1 | Art. 2 | Art. 3 | Art. 4 | Art. 5 |
| No. 1 | 7.4 | 22.8 | 15.3 | 17.2 | 22.5 |
| No. 2 | 18.3 | 60.9 | 38.8 | 43.2 | 33.4 |
| No. 3 | 29.6 | 81.6 | 62.8 | 67.1 | 56.1 |

The results show that Article 1 exhibited the shortest absorption time at all three wettings. Article 1 comprised a acquisition layer made of a plurality of fragments of Foam XII. The acquisition layer in Article 1 was arranged between a liquid permeable top sheet and a storage layer.

Example 3—Estimation of the Rewetting

The rewetting, i.e., how wet a top sheet of an absorbent article is after wetting, has been measured for three absorbent articles.

The top sheet of all three tested articles was constituted of a carded nonwoven material of polypropylene having a grammage of 23 g/cm². The manufacturer of the top sheet is JW Suominen OY. The storage material in all three tested articles was constituted of five layers of a reference filter paper denoted ERT FF3 from Hollingsworth Vose Company Ltd. Test liquid for all test samples was a solution containing 9 percent by weight of NaCl.

The first tested absorbent article comprised an acquisition layer constituted of a plurality of fragments of Foam XII. The width of the fragments was 5 mm ands the length of the fragments was 5 mm. The total weight of the fragments was 1.0 grams.

The second tested absorbent article comprised an acquisition layer constituted of a plurality of fragments of a compressed foam material from regenerated cellulose from Polyform GmbH. The width of the fragments was 7 mm and the length of the fragments was 7 mm. The total weight of the fragments was 1.0 grams.

The third tested absorbent article did not comprise any acquisition layer at all.

TABLE 3

| Article | Rewetting (grams) |
|---|---|
| No. 1 | 0.10 |
| No. 2 | 1.46 |
| No. 3 | 0.13 |

The results show that Article 1 provided the lowest rewetting. Article 1 comprised an acquisition layer being constituted of fragments of the polyacrylate-based foam material Foam XII.

The above-described embodiments are merely illustrative and are in no way intended to limit the present invention, which is only limited by the following claims.

What is claimed is:

1. An absorbent article comprising:
a liquid-permeable upper surface; and
an absorbent structure having a planar extension;
wherein the absorbent structure comprises an acquisition layer and at least one storage layer;
wherein the acquisition layer comprises a plurality of fragments of a liquid-absorbing, open-celled, polyacrylate-based foam material;
wherein each fragment has a planar extension having a transversal direction and a longitudinal direction, and a thickness direction extending perpendicularly to the planar extension of the fragment;
wherein the width in the transversal direction of each fragment in a dry condition does not exceed 10 millimeters;
wherein the total area of the fragments in dry condition in the planar extension is lower than the area of the absorbent structure in the planar extension; and
at least most of the fragments are arranged such that they are not touching adjacent fragments wherein at least most of the fragments are separated by spaces;
for each fragment, a distance to an adjacent one of the fragments is at least two times the width of the fragment;
for each fragment, said distance to an adjacent one of the fragments is not larger than five times the width of the fragment;
each fragment is highly compressed in a dry condition;
each fragment is dimensioned and configured such that upon wetting, either the volume of the fragment increases by at least 500%, or the area in the planar extension of the fragment increases by at least 300%; and
each fragment expands in three dimensions upon wetting.

2. The absorbent article according to claim 1, wherein each fragment in a dry condition has a length in the transversal direction which does not exceed 7 millimeters.

3. The absorbent article according to claim 1, wherein each fragment in a dry condition has a length in the longitudinal direction which does not exceed 20 millimeters.

4. The absorbent article according to claim 1, wherein the total area of the fragments in the planar extension of the fragment maximally is 50% of the total area of the absorbent structure in the planar extension.

5. The absorbent article according to claim 1, wherein the total area of the fragments in the planar extension of the fragment maximally is 30% of the total area of the absorbent structure in the planar extension of the absorbent structure.

6. An absorbent article comprising:
a liguid-permeable upper surface; and
an absorbent structure having a planar extension;
wherein the absorbent structure comprises an acguisition layer and at least one storage layer;
wherein the acquisition layer comprises a plurality of fragments of a liquid-absorbing, open-celled. polyacrylate-based foam material;
wherein each fragment has a planar extension having a transversal direction and a longitudinal direction, and a thickness direction extending perpendicularly to the planar extension of the fragment;
wherein the width in the transversal direction of each fragment in a dry condition does not exceed 10 millimeters;
wherein the total area of the fragments in dry condition in the planar extension is lower than the area of the absorbent structure in the planar extension; and
wherein each fragment in a dry condition has a density of at least 0.18 g/cm³ wherein at least most of the fragments are separated by spaces;
for each fragment, a distance to an adjacent one of the fragments is at least two times the width of the fragment;
for each fragment, said distance to an adjacent one of the fragments is not larger than five times the width of the fragment;

each fragment is highly compressed in a dry condition;

each fragment is dimensioned and configured such that upon wetting, either the volume of the fragment increases by at least 500%, or the area in the planar extension of the fragment increases by at least 300%; and each fragment expands in three dimensions upon wetting.

7. The absorbent article according to claim 1, wherein the fragments are applied against the upper surface of the storage layer in a wetting area.

8. The absorbent article according to claim 1, wherein at least one of the storage layers comprises cellulosic fibers and particulate superabsorbent, wherein an amount of superabsorbent material calculated on the total weight of the storage layer in dry condition is at least 50 percent by weight.

9. The absorbent article according to claim 1, wherein at least one of the storage layers comprises cellulosic fibers and particulate superabsorbent, wherein a amount of superabsorbent material calculated on the total weight of the storage layer in dry condition is at least 70 percent by weight.

10. The absorbent article according to claim 1, wherein the absorbent article is a diaper, an incontinence guard, or a sanitary napkin.

* * * * *